(12) United States Patent
Boumsell et al.

(10) Patent No.: US 8,679,500 B2
(45) Date of Patent: Mar. 25, 2014

(54) COMPOSITIONS CONTAINING ANTIBODIES FOR TREATING CD5+ HLA-DR+ B OR T CELL RELATED DISEASES

(75) Inventors: Laurence Boumsell, Paris (FR); Christian Berthou, Brest Cedex (FR); Karine Lester, Brest Cedex (FR); Severine Loisel, Brest Cedex (FR); Martine Cerruti, Saint Christol les Ales (FR)

(73) Assignees: Institute National de la Sante et de la Recherche Medicale (INSERM), Paris (FR); Universite de Bretagne Occidentale, Brest (FR); Centre National de la Recherche Scientifique (CNRS), Paris (FR)

( * ) Notice: Subject to any disclaimer, the term of this patent is extended or adjusted under 35 U.S.C. 154(b) by 0 days.

(21) Appl. No.: 13/320,097

(22) PCT Filed: May 14, 2010

(86) PCT No.: PCT/EP2010/056664
§ 371 (c)(1),
(2), (4) Date: Jan. 23, 2012

(87) PCT Pub. No.: WO2010/145895
PCT Pub. Date: Dec. 23, 2010

(65) Prior Publication Data
US 2012/0121598 A1    May 17, 2012

(30) Foreign Application Priority Data
May 14, 2009  (EP) ..................................... 09305434

(51) Int. Cl.
*A61K 39/395* (2006.01)
*A61K 39/00* (2006.01)
*C07K 16/28* (2006.01)
*C07K 16/30* (2006.01)

(52) U.S. Cl.
USPC ................. 424/144.1; 424/133.1; 424/153.1; 424/154.1; 424/155.1; 424/156.1; 424/173.1; 424/174.1; 530/387.3; 530/388.22; 530/388.73; 530/388.75; 530/388.8; 530/389.6; 530/389.7

(58) Field of Classification Search
None
See application file for complete search history.

(56) References Cited

U.S. PATENT DOCUMENTS

2006/0210475 A1 * 9/2006 Goldenberg et al. ........ 424/1.49

FOREIGN PATENT DOCUMENTS

DE     101 62 870 A1   7/2003
EP     1 479 760 A1    11/2004

OTHER PUBLICATIONS

Healthline.com, "Non-hodgkin's Lymphoma: In Depth-Overview", pp. 1-3, http://www.healthline.com/channel/non-hodgkins-lymphoma_indepth-overview, retrieved Dec. 2, 2008.*
Rudikoff et al. "Single amino acid substitution altering antigen binding specificity", Proceedings of the National Academy of Sciences, 1982. vol. 79, pp. 1979-1983.*
MacCallum et al. "Antibody-antigen interactions: contact analysis and binding site topography", Journal of Molecular Biology, 1996. vol. 262, pp. 732-745.*
De Pascalis et al."Grafting of abbreviated complementarity determining regions containing specificity determining residues essential for ligand contact to engineer a less immunogenic humanzied monoclonal antibody", Journal of Immunology, 2002. vol. 169, pp. 3076-3084.*
Gary-Gouy et al.,"Natural Phosphorylation of CD5 in Chronic Lymphocytic Leukemia B Cells and Analysis of CD5-Regulated Genes in a B Cell Line Suggest a Role for CD5 in Malignant Phenotype", The Journal of Immunology, 2007, 179: 4335-4344.*

* cited by examiner

*Primary Examiner* — Ron Schwadron
(74) *Attorney, Agent, or Firm* — Whitham, Curtis, Christofferson & Cook, P.C.

(57) ABSTRACT

The present invention relates to compositions containing antibodies for treating CD5+ HLA-DR+ B OR T cell related diseases such as B or T cell malignances (leukaemia and lymphoma), autoimmune diseases and T cell related diseases as transplantation and graft rejection.

10 Claims, 1 Drawing Sheet

SEQUENCE LISTING

```
<160> NUMBER OF SEQ ID NOS: 16

<210> SEQ ID NO 1
<211> LENGTH: 107
<212> TYPE: PRT
<213> ORGANISM: artificial sequence
<220> FEATURE:
<223> OTHER INFORMATION: anti-CD5 light chain

<400> SEQUENCE: 1

Asp Ile Gln Val Thr Gln Ser Pro Ser Ser Leu Ser Ala Ser Leu Gly
1               5                   10                  15

Glu Arg Ile Ser Leu Thr Cys Arg Thr Ser Gln Asp Ile Ser Asn Tyr
            20                  25                  30

Leu Asn Trp Phe Gln Gln Lys Pro Asp Gly Thr Phe Lys Arg Leu Ile
        35                  40                  45

Tyr Ala Thr Ser Ser Leu Asp Ser Gly Val Pro Lys Arg Phe Ser Gly
    50                  55                  60

Ser Gly Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Phe
                85                  90                  95

Thr Phe Gly Ser Gly Thr Lys Leu Glu Ile Lys
            100                 105

<210> SEQ ID NO 2
<211> LENGTH: 118
<212> TYPE: PRT
<213> ORGANISM: artificial sequence
<220> FEATURE:
<223> OTHER INFORMATION: anti-CD5 heavy chain

<400> SEQUENCE: 2

Glu Val Gln Leu Gln Glu Ser Gly Pro Gly Leu Val Lys Pro Ser Gln
1               5                   10                  15

Thr Leu Ser Leu Thr Cys Ser Val Thr Gly Tyr Ser Ile Thr Ser Gly
            20                  25                  30

Tyr Tyr Trp His Trp Ile Arg Gln Phe Pro Gly Asn Lys Leu Glu Trp
        35                  40                  45

Met Gly Tyr Ile Ser Tyr Ser Gly Phe Thr Asn Tyr Lys Thr Ser Leu
```

```
                50                  55                  60
Ile Asn Arg Ile Ser Ile Thr His Asp Thr Ser Glu Asn Gln Phe Phe
65                  70                  75                  80

Leu Asn Leu Asn Ser Val Thr Thr Glu Asp Thr Ala Thr Tyr Tyr Cys
                85                  90                  95

Ala Gly Asp Arg Thr Gly Ser Trp Phe Ala Tyr Trp Gly Gln Gly Thr
                100                 105                 110

Leu Val Thr Val Ser Ala
        115

<210> SEQ ID NO 3
<211> LENGTH: 6
<212> TYPE: PRT
<213> ORGANISM: artificial sequence
<220> FEATURE:
<223> OTHER INFORMATION: anti-CD5 light chain CDR1 (L1)

<400> SEQUENCE: 3

Gln Asp Ile Ser Asn Tyr
1               5

<210> SEQ ID NO 4
<211> LENGTH: 3
<212> TYPE: PRT
<213> ORGANISM: artificial sequence
<220> FEATURE:
<223> OTHER INFORMATION: anti-CD5 light chain CDR2 (L2)

<400> SEQUENCE: 4

Ala Thr Ser
1

<210> SEQ ID NO 5
<211> LENGTH: 9
<212> TYPE: PRT
<213> ORGANISM: artificial sequence
<220> FEATURE:
<223> OTHER INFORMATION: anti-CD5 light chain CDR3 (L3)

<400> SEQUENCE: 5

Leu Gln Tyr Ala Ser Tyr Pro Phe Thr
1               5

<210> SEQ ID NO 6
<211> LENGTH: 9
<212> TYPE: PRT
<213> ORGANISM: artificial sequence
<220> FEATURE:
<223> OTHER INFORMATION: anti-CD5 heavy chain CDR1 (H1)

<400> SEQUENCE: 6

Gly Tyr Ser Ile Thr Ser Gly Tyr Tyr
1               5

<210> SEQ ID NO 7
<211> LENGTH: 7
<212> TYPE: PRT
<213> ORGANISM: artificial sequence
<220> FEATURE:
<223> OTHER INFORMATION: anti-CD5 heavy chain CDR2 (H2)

<400> SEQUENCE: 7

Ile Ser Tyr Ser Gly Phe Thr
1               5
```

```
<210> SEQ ID NO 8
<211> LENGTH: 11
<212> TYPE: PRT
<213> ORGANISM: artificial sequence
<220> FEATURE:
<223> OTHER INFORMATION: anti-CD5 heavy chain CDR3 (H3)

<400> SEQUENCE: 8

Ala Gly Asp Arg Thr Gly Ser Trp Phe Ala Tyr
1               5                   10

<210> SEQ ID NO 9
<211> LENGTH: 107
<212> TYPE: PRT
<213> ORGANISM: artificial sequence
<220> FEATURE:
<223> OTHER INFORMATION: anti-HLA-DR light chain

<400> SEQUENCE: 9

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ser Leu His Ser Gly Val Pro Ser Arg Phe Ser Gly
50                  55                  60

Ser Gly Ser Gly Thr Asp Tyr Ser Leu Thr Ile Ser Asn Leu Glu Pro
65                  70                  75                  80

Glu Asp Ile Gly Thr Tyr Tyr Cys Gln Gln Tyr Ser Lys Leu Pro Trp
                85                  90                  95

Thr Phe Gly Gly Gly Thr Lys Leu Glu Ile Lys
            100                 105

<210> SEQ ID NO 10
<211> LENGTH: 118
<212> TYPE: PRT
<213> ORGANISM: artificial sequence
<220> FEATURE:
<223> OTHER INFORMATION: anti-HLA-DR heavy chain

<400> SEQUENCE: 10

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ile Phe Thr Asn Tyr
            20                  25                  30

Gly Met Asn Trp Val Lys Gln Val Pro Gly Lys Gly Leu Lys Trp Met
        35                  40                  45

Ala Trp Ile Asn Thr Tyr Asn Gly Glu Pro Thr His Ala Asp Asp Phe
50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Gly Asp Tyr Tyr Gly Tyr Glu Asp Tyr Trp Gly Gln Gly Thr
            100                 105                 110

Ser Val Thr Val Ser Ser
        115

<210> SEQ ID NO 11
<211> LENGTH: 6
```

```
<212> TYPE: PRT
<213> ORGANISM: artificial sequence
<220> FEATURE:
<223> OTHER INFORMATION: anti-HLA-DR light chain CDR1 (L1)

<400> SEQUENCE: 11

Gln Gly Ile Ser Asn Tyr
1               5

<210> SEQ ID NO 12
<211> LENGTH: 3
<212> TYPE: PRT
<213> ORGANISM: artificial sequence
<220> FEATURE:
<223> OTHER INFORMATION: anti-HLA-DR light chain CDR2 (L2)

<400> SEQUENCE: 12

Tyr Thr Ser
1

<210> SEQ ID NO 13
<211> LENGTH: 9
<212> TYPE: PRT
<213> ORGANISM: artificial sequence
<220> FEATURE:
<223> OTHER INFORMATION: anti-HLA-DR light chain CDR3 (L3)

<400> SEQUENCE: 13

Gln Gln Tyr Ser Lys Leu Pro Trp Thr
1               5

<210> SEQ ID NO 14
<211> LENGTH: 8
<212> TYPE: PRT
<213> ORGANISM: artificial sequence
<220> FEATURE:
<223> OTHER INFORMATION: anti-HLA-DR heavy chain CDR1 (H1)

<400> SEQUENCE: 14

Gly Tyr Ile Phe Thr Asn Tyr Gly
1               5

<210> SEQ ID NO 15
<211> LENGTH: 8
<212> TYPE: PRT
<213> ORGANISM: artificial sequence
<220> FEATURE:
<223> OTHER INFORMATION: anti-HLA-DR heavy chain CDR2 (H2)

<400> SEQUENCE: 15

Ile Asn Thr Tyr Asn Gly Glu Pro
1               5

<210> SEQ ID NO 16
<211> LENGTH: 11
<212> TYPE: PRT
<213> ORGANISM: artificial sequence
<220> FEATURE:
<223> OTHER INFORMATION: anti-HLA-DR heavy chain CDR3 (H3)

<400> SEQUENCE: 16

Ala Arg Gly Asp Tyr Tyr Gly Tyr Glu Asp Tyr
1               5                   10
```

COMPOSITIONS CONTAINING ANTIBODIES FOR TREATING CD5+ HLA-DR+ B OR T CELL RELATED DISEASES

The present invention relates to compositions and methods for preventing and treating CD5$^+$ HLA-DR$^+$ B or T cell related diseases, such as B or T cell malignancies, autoimmune diseases, transplantation diseases and graft rejections.

The Cluster of Differentiation 5 (CD5) is a 67 kDa type I glycoprotein, member of the Scavenger Receptor Cysteine-Rich (SRCR) superfamily. CD5 is primarily found on T Lymphocytes and on a subset of IgM secreting B cells called B1a cells. Its role is not clearly defined but it seems to participate in immune tolerance as a regulator of antigen receptor (TCR/BCR) signaling and activation. Recently it was described that the CD5 ectodomain interacts with conserved fungal cell wall components. Moreover previous data implicated CD5 in negative regulation of lymphocyte antigen receptor signalling by increasing the threshold of antigen stimulation. CD5 thus protects normal human B cells from apoptosis after BCR stimulation while reducing the BCR-induced Ca(2$^+$) response. It was also shown that CD5 protects T cell from activation induced cell death and supports the survival of B cells by stimulating IL-10 production and by concurrently exerting negative feedback on BCR-induced signaling events that can promote cell death. CD5 is overexpressed on CLL and is one of the parameters required for the diagnosis of CLL according to WHO criteria. Several anti-CD5 mAbs, like the murine IgG$_{2a}$ CD5 antibodies T101 and anti-Leu-1 have already been tested in patients for therapeutic purpose, mostly in T cell maligancies. However response to murine anti-Leu-1 (Miller et al. (1983) *Blood* 62(5):988-95) and murine T101, either in unconjugated form (Dillman et al. (1984) *J Clin Oncol* 2(8):881-891) or conjugated to toxins (Hertler et al. (1988) *J Biol Response Mod* 7(1):97-113) or radioisotopes (Foss et al. (1998) *Clin Cancer Res* 4(11):2691-700) resulted in mitigated clinical benefit or response was of short duration.

Monoclonal antibodies (mAb) are already successfully used in different treatments of cancer, hematopoietic malignancies, autoimmune diseases and transplantation. mAbs can be used in the form of naked unmodified antibodies or conjugated to radioactive elements or toxins. The well-known anti-CD20 Rituximab (MABTHERA, RITUXAN) and anti-CD52 alemtuzumab (Campath-1 H) mAbs have been extensively studied in patients at various clinical stages in B-cell Non-Hodgkin Lymphoma (NHL) and Chronic Lymphocytic Leukaemia (CLL) and are now widely approved not only in the treatment of B-cell malignancies but also for autoimmune diseases. Other mAbs directed against cell surface CD molecules expressed by tumor cells (CD19, CD22, CD23, CD40, CD80, HLA-DR) or antigen over-expressed in tumour cells (CD71) are currently in clinical trial or in development.

The CD71 receptor is a 95 kD type II transmembrane glycoprotein also known as the transferrin receptor. CD71 is involved in the cellular uptake of iron and in the regulation of cell growth. Interestingly, different studies suggest that malignant tissue express the CD71 receptor at a higher level when compared to their normal counterpart. Moreover, Chronic Lymphocytic Leukaemia (CLL) and NHL present an expression of transferrin receptor increasing with the clinical grade stage of the tumour. Among several other mAbs, the murine monoclonal IgA antibody 42/6 directed against human CD71 demonstrated potent cytotoxic effects on haematopoietic tumour cells (Taetle et al (1983) *Int J Cancer* 32(3):343-9). After the promising results observed in vitro, a phase I clinical trial was conducted on 27 patients with various refractory and advanced cancers (Brooks et al. (1995) *Clin Cancer Res* 1(11):1259-65). The intravenous infusions treatment showed little toxicity effects. However, due to the rapid clearance of the murine IgA antibody, only three patients demonstrated partial anti-tumour response. This underlines the need of antibodies of different isotypes, as well as chimeric, humanized or human mAb. A recent chimeric CD71 antibody called D2C has been described to induce apoptosis and cell cycle arrest in 01 phase in vitro (Qing et al. (2006) *Cancer Immunol Immunother* 55(9):1111-21).

The human leukocyte antigen HLA-DR is a class II major histocompatibility complex (MHC) antigen which is involved in the presentation of exogenous antigens to CD4+ helper T cells in order to initiate immune response. HLA-DR is expressed on immune cells including B cells, activated T lymphocytes, monocytes and dendritic cells, and at high level on B lymphoid Leukaemia. Several studies showed the ability of anti-HLA-DR antibodies to induce cell death in vitro and to inhibit tumour growth in vivo. It is still controversial what signalling pathways leading to apoptosis are involved with some studies noting direct cell death, others involving caspase activation via Fas and others a caspase independence pathway.

It is also unclear how tumour specific are these antibodies as some studies showed selective effect on resting (Newell et al. (1993) Proc Natl Acad Sci USA 8(1):34-47) or on the contrary, on activated (Truman et al (1994) Int Immunol 6(6):887-96) B-cells, or on neoplastic cells (Vidovic et al. (1998) Cancer Lett 128(2):127-35). All these differences in response could be the consequence of the use of different antibodies (e.g. murine or humanized) or of the recognized epitope (alpha/beta chain). Two anti-HLA-DR mAb have been introduced in clinical trials for the treatment of NHL: Lym-1 and Hu1D10. The radiolabeled murine IgG2a Lym-1 showed promising preliminary results, with increased survival in patients with NHL and with CLL (DeNardo et al (1997) Cancer 80(12 suppl.): 2706-11). However these results were not confirmed. H1 D10 is a humanized antibody which, like Lym-1, binds to a variant of the HLA-DR chain. H1D10 has been evaluated in patients with relapsed or refractory indolent NHL where minimal toxicity and early response have been observed (Brown et al (2001) Clin Lymphoma 2(3):188-90). However, phase II clinical trials were disappointing. Combinations of Hu1D10 and Rituximab have been recently evaluated with mitigated results (Dunleavy et al. (2005) J Clin Oncol Meeting abstract 23(16 suppl.): 6607)

Accordingly, it is an object of the present invention to provide alternative and improved compositions and methods to treat CD5$^+$ HLA-DR$^+$ B or T cell related diseases.

DESCRIPTION OF THE INVENTION

In this regards, the present invention arises from the finding by the inventors that the co-injection of anti-HLA-DR and anti-CD5 antibodies to mice previously injected with cells which mimic B-CLL and mantle cell lymphoma increased mice survival.

Accordingly, the present invention relates to at least one CD5 binding molecule and at least one HLA-DR binding molecule for use as a medicament in the prevention or treatment of CD5$^+$ HLA-DR$^+$ B or T cell related diseases.

As intended herein, the expression "CD5 binding molecule and HLA-DR binding molecule" may refer to either two distinct molecules, one able to bind to CD5 and the other able to bind to HLA-DR or to a single molecule able to recognize both CD5 and HLA-DR.

Preferably, the CD5 binding molecule and the HLA-DR binding molecule of the invention, upon binding to CD5 and HLA-DR on a B or a T cell, are liable to destroy or deplete B and T cells in a subject and/or interfere with one or more B cell and T cell functions, e.g. by reducing or preventing a humoral response elicited by the B cell or T cell. The CD5 binding molecules and HLA-DR binding molecules are preferably used to deplete CD5$^+$ B cells (i.e. reduce circulating CD5$^+$ B cell levels) in a subject treated therewith. Such depletion may be achieved via various mechanisms such as antibody-dependent cell mediated cytotoxicity (ADCC), antibody dependent phagocytosis (ADP) and/or complement dependent cytotoxicity (CDC), inhibition of cell proliferation and/or induction of cell death (e.g. via apoptosis).

"Binding molecules" included within the scope of the present invention notably include antibodies, synthetic or native sequence peptides and small molecule antagonists which bind to the cell surface molecules CD5 or HLA-DR, optionally conjugated with or fused to a cytotoxic agent.

Preferably, the CD5 binding molecule and the HLA-DR binding molecule as defined above are antibodies respectively directed against CD5 and HLA-DR, more preferably monoclonal antibodies.

Also preferably, the at least one CD5 binding molecule and at least one HLA-DR binding molecule as defined above can be constitutive of a bispecific antibody.

Preferably, these antibodies are specific respectively for CD5 and HLA-DR. Specificity, as used herein, refers to the ability of an antibody to distinguish between CD5 or HLA-DR, optionally glycosylated, and any other polypeptides, based on their structural difference, such that the recognition upon the target protein is unique to a reasonable degree.

As used herein the terms "antibody" and "immunoglobulin" have the same meaning and are used in the broadest sense and specifically covers intact monoclonal antibodies, polyclonal antibodies, chimeric, humanized or human antibodies, antibodies, diabodies, multispecific antibodies (e.g. bispecific antibodies) formed from at least two intact antibodies, and also antibody fragments.

Antibodies according to invention may be produced by any technique known in the art, such as, without limitation, any chemical, biological, genetic or enzymatic technique, either alone or in combination.

Knowing the amino acid sequence of an antibody, one skilled in the art can readily produce said antibody, by standard techniques for production of polypeptides or glycosylated polypeptides. For instance, they can be synthesized using well-known solid phase method, preferably using a commercially available peptide synthesis apparatus (such as that made by Applied Biosystems, California) and following the manufacturer's instructions.

Alternatively, antibodies of the invention can be produced by recombinant DNA technology in a suitable expression system. The term "expression system" means a host cell and compatible vector under suitable conditions, e.g. for the expression of a protein coded by foreign DNA carried by the vector and introduced to the host cell. Typically, a nucleic acid sequence encoding an antibody, in particular a monoclonal antibody, of the invention, or a fragment thereof, may be included in any suitable expression vector which may then be introduced into any suitable eukaryotic or prokaryotic hosts that will express the desired antibodies.

In natural antibodies, two heavy chains are linked to each other by disulfide bonds and each heavy chain is linked to a light chain by a disulfide bond. There are two types of light chain, lambda ($\lambda$) and kappa ($\kappa$). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine antigen binding site and thus the recognition and specificity to the antigen. The constant region domains of the light (VL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain.

The term "monoclonal antibody" or "mAb" as used herein refers to an antibody molecule of a single amino acid composition, that is directed against a specific antigen and which may be produced by a single clone of B cells or hybridoma. Monoclonal antibodies may also be recombinant, i.e. obtained by protein engineering and next produced in a mammalian cell line such as CHO, NSO, PERC6 or any other cell after transfection.

The term "chimeric antibody" refers to an engineered antibody which comprises a VH domain and a VL domain of an antibody derived from a non-human animal, in association with a CH domain and a CL domain of another antibody, in particular a human antibody. The non-human animal may be a mouse, a rat, a hamster, a rabbit or the like.

The expression "bispecific antibody" refers to an engineered antibody which possess two different antigen binding sites. In a preferred embodiment of the invention, the at least one CD5 binding molecule and at least one HLA-DR binding molecule of the invention is a bispecific antibody which is able to bind to CD5 and to HLA-DR.

The term "diabodies" refers to small antibody fragments with two antigen-binding sites, which fragments comprise a heavy-chain variable domain (VH) connected to a light-chain variable domain (VL) in the same polypeptide chain (VH-VL). In general, by using a linker that is too short to allow pairing between the two domains on the same chain, the domains are forced to pair with the complementary domains of another chain and create two antigen-binding sites. Preferably the diabody is able to recognize CD5 and HLA-DR.

The expression "humanized antibody" preferably refers to antibodies in which the framework or "complementarity determining regions" (CDR) have been modified to comprise the CDR from a donor immunoglobulin of different specificity as compared to that of the parent immunoglobulin. In a preferred embodiment, a mouse CDR is grafted into the framework region of a human antibody to prepare the "humanized antibody". The antibodies of the invention are preferably "humanized antibodies".

The expression "human antibody" preferably refers to fully human antibodies that have been 1) prepared by immunization in mice with a human immunoglobulin gene repertoire, or 2) prepared by immunization in various strains of immunodeficient mice reconstituted with human immune/hematopoietic cells or 3) to human antibodies isolated from B cells of immunized individuals and EBV transformed or 4) from combination of genes obtained from human VH and VL libraries.

The expression "antibody fragments" comprise a portion of an intact antibody, preferably the antigen binding or variable region of the intact antibody. Examples of antibody fragments include Fv, Fab, F(ab')$_2$, Fab', dsFv, scFv, sc(Fv)$_2$, diabodies and multispecific antibodies formed from antibody fragments.

In an embodiment of the invention, the at least one CD5 binding molecule as defined above is an antibody comprising at least one CDR which sequence is selected from within SEQ ID NO: 1 or SEQ ID NO: 2.

SEQ ID NO: 1 and SEQ ID NO: 2 respectively correspond to the amino-acid sequence of the light chain and the heavy chain of an anti-CD5 antibody.

In an embodiment of the invention, the at least one HLA-DR binding molecule as defined above is an antibody comprising at least one CDR which sequence is selected from within SEQ ID NO: 9 or SEQ ID NO: 10.

SEQ ID NO: 9 and SEQ ID NO: 10 are respectively correspond to the amino-acid sequence of the light chain and the heavy chain of an anti-HLA-DR antibody.

As is well known to one of skill in the art, the specificity of the antibody lies in the structural complementarity between the antibody combining site and the antigenic determinant. Antibody combining sites are made up of residues that are primarily from the hypervariable or complementarity determining regions (CDRs). Occasionally, residues from non hypervariable or framework regions (FR) influence the overall domain structure and hence the combining site. Complementarity determining regions (CDRs) refer to amino acid sequences which, together, define the binding site and the affinity and specificity of the natural Fv region of a native immunoglobulin binding-site. The light and heavy chains of an immunoglobulin each have three CDRs, designated L-CDR1 (L1), L-CDR2 (L2), L-CDR3 (L3) and H-CDR1 (H1), H-CDR2 (H2), H-CDR3 (H3), respectively. Therefore, an antigen-binding site includes six CDRs, comprising the CDR set from each of a heavy and a light chain V region.

The expression "Framework Regions" (FRs) refers to amino acid sequences interposed between CDRs, i.e. to those portions of immunoglobulin light and heavy chain variable regions that are relatively conserved among different immunoglobulins in a single species, as defined by IMGT (Lefranc et al. (2009) *Nucl. Acids Res* 37:D1006-D1012, Brochet et al. (2008) *Nucl Acids Res* 36:W503-508, Kabat et al. (1991) Sequences of Proteins of Immunological Interest, National Institutes of Health, Bethesda, Md.).

As used herein, a "human framework region" is a framework region presenting a sequence identity of at least 85%, 90%, 95%, or of 100% with the framework region of a naturally occurring human antibody.

As intended herein, the expression "selected from within SEQ ID NO: X" means that the CDR sequence is a portion of SEQ ID NO: X. The CDR sequences can easily be identified by the person skilled in the art. Numerous methods are known in the art such as the IGMT (ImMunoGeneTics information system) method, notably described by Lefranc et al. ((2009) *Nucl. Acids Res* 37:D1006-D1012), Brochet et al. ((2008) *Nucl Acids Res* 36:W503-508) and Kabat et al. ((1991) Sequences of Proteins of Immunological Interest, National Institutes of Health, Bethesda, Md.)).

For example, when the IGMT method is applied to SEQ ID NO: 1, the CDR corresponding to SEQ ID NO: 3, SEQ ID NO: 4 and SEQ ID NO: 5 are identified. Similarly, when the IGMT method is applied to SEQ ID NO: 2, the CDR corresponding to SEQ ID NO: 6, SEQ ID NO: 7 and SEQ ID NO: 8 are identified. When the IGMT method is applied to SEQ ID NO: 9, the CDR corresponding to SEQ ID NO: 11, SEQ ID NO: 12 and SEQ ID NO: 13 are identified. Finally, when the IGMT method is applied to SEQ ID NO: 10, the CDR corresponding to SEQ ID NO: 14, SEQ ID NO: 15 and SEQ ID NO: 16 are identified.

Thus, in another embodiment of the invention, the CD5 binding molecule as defined above is an antibody comprising:

(i) a variable light chain comprising at least one CDR represented by a sequence selected from the group consisting of SEQ ID NO: 3, SEQ ID NO: 4, SEQ ID NO: 5 and/or (ii) a variable heavy chain comprising at least one CDR represented by a sequence selected from the group consisting of SEQ ID NO: 6, SEQ ID NO: 7, SEQ ID NO: 8.

Similarly, in another embodiment of the invention, the HLA-DR binding molecule as defined above is an antibody comprising:

(i) a variable light chain comprising at least one CDR represented by a sequence selected from the group consisting of SEQ ID NO: 11, SEQ ID NO: 12, SEQ ID NO: 13 and/or (ii) a variable heavy chain comprising at least one CDR represented by a sequence selected from the group consisting of SEQ ID NO: 14, SEQ ID NO: 15, SEQ ID NO: 16.

In another preferred embodiment of the invention, the CD5 binding molecule as defined above is an antibody comprising a variable light chain of SEQ ID NO: 1 and/or a variable heavy chain of SEQ ID NO: 2.

Similarly, in another preferred embodiment of the invention, the HLA-DR binding molecule as defined above is an antibody comprising a variable light chain of SEQ ID NO: 9 and/or a variable heavy chain of SEQ ID NO: 10.

"CD5$^+$ HLA-DR$^+$ B or T cell related diseases" as intended herein relate to any pathology involving CD5$^+$ HLA-DR$^+$ B or T cells. Such pathologies can be due to an aberrant CD5$^+$ HLA-DR$^+$ B cell activity that deviates from the normal, proper, or expected course in a subject. For example, aberrant CD5$^+$ HLA-DR$^+$ B cell activity may include inappropriate proliferation of cells which DNA or other cellular components have become damaged or defective. Aberrant CD5$^+$ HLA-DR$^+$ B cell activity may include cell proliferation whose characteristics are associated with a disease caused by, mediated by, or resulting in inappropriately high levels of cell division, inappropriately low levels of apoptosis, or both. Such diseases may be characterized, for example, by single or multiple local abnormal proliferations of cells, groups of cells or tissue(s), whether cancerous or noncancerous, benign or malignant. Aberrant CD5$^+$ HLA-DR$^+$ B cell activity may also include aberrant antibody production, such as production of autoantibodies, or overproduction of antibodies typically desirable when produced at normal levels. It is contemplated that aberrant HLA-DR$^+$ CD5+ B cell activity may occur in certain subpopulations of B-cells and not in other subpopulations. Aberrant CD5$^+$ HLA-DR$^+$ B cell activity may also include inappropriate stimulation of T-cells, such as by inappropriate CD5$^+$ HLA-DR$^+$ B cell antigen presentation to T-cells or by other pathways involving B cells. Alternatively, CD5$^+$ HLA-DR$^+$ T cell diseases can result from unwanted stimulation of donor T cells such as one encounter during graft versus host diseases or activation of host T cell after transplantation.

Preferably, the CD5$^+$ HLA-DR$^+$ B or T cell related disease as defined above is selected in the group consisting of B or T cell malignancies, B or T cell auto-immune diseases or transplantation diseases and graft rejections.

Preferably, the B or T cell malignancies as defined above is selected from the group consisting of B cell chronic lymphocytic leukaemia, mantle cell lymphoma, some diffuse large B cell lymphoma, T cell chronic lymphocytic leukaemia, Adult T cell Leukemia (ATL).

Preferably, the B or T cell autoimmune diseases as defined above is selected from the group consisting of rhumatoïd arthritis, psoriasis, systemic lupus erythematosus, Castelman's disease, chronic thyroiditis (Hashimoto's thyroiditis) multiple sclerosis (MS).

Preferably, the B or T cell diseases as defined above is a T cell related diseases as graft versus host diseases for example, after bone marrow transplantation or activation of host T cell after graft rejections, such as after kidney transplantation.

In the context of the invention, the term "treating" or "treatment" means reversing, alleviating, inhibiting the progress of, or preventing the disorder or condition to which such term applies, or one or more symptoms of such disorder or condition. In particular, the treatment of the disorder may consist in destroying or depleting $CD5^+$ $HLA-DR^+$ B or T cells. Most preferably, such treatment leads to the complete depletion of $CD5^+$ $HLA-DR^+$ B or T cells.

According to the invention, the term "subject" or "individual" to be treated is intended for a human or non-human mammal (such as a rodent (mouse, rat), a feline, a canine, or a primate) affected or likely to be affected with $CD5^+$ $HLA-DR^+$ B or T cell related diseases. Preferably, the subject is a human.

In a preferred embodiment of the invention, the at least one CD5 binding molecules and at least one HLA-DR binding molecule as define above is combined with at least one other compound for the treatment of B or T cell malignancies, autoimmune diseases or transplantation diseases and graft rejections.

Preferably, the at least one other compound for the treatment of malignancies is an anti-CD20 (RITUXIMAB).

Preferably, the at least one other compound for the treatment of autoimmune diseases is an anti-CD20 (RITUXIMAB).

Preferably, the at least one other compound for the treatment of transplantation diseases and graft rejections is an anti-CD3 monoclonal antibody.

The invention also relates to a pharmaceutical composition comprising at least one CD5 binding molecule as defined above and at least one HLA-DR binding molecule as defined above.

Preferably the pharmaceutical composition also comprises a pharmaceutically acceptable carrier.

More preferably the pharmaceutical composition further comprises at least one other compound for the treatment of B or T cell malignancies, autoimmune diseases or transplantation diseases and graft rejections as define above.

The expression "pharmaceutically acceptable carrier" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can notably be formulated for an intravenous, intramuscular, subcutaneous, and the like.

Preferably, the pharmaceutical compositions of the invention contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

To prepare pharmaceutical compositions, an effective amount of the antibody may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. The form is preferably sterile and is fluid to the extent that easy syringability exists. It is preferably stable under the conditions of manufacture and storage and is preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An antibody of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions can be prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

By way of example, the antibodies of the invention may be administered at a concentration of about 0.001 to 1000 mg/kg body weight or about 0.01 to 500 mg/kg body weight or about 1 to 200 mg/kg body weight or about 1 to 100 mg/kg body weight or about 10 mg/kg body weight.

The invention also relates to a product containing:
a CD5 binding molecule as defined above,
an anti-HLA-DR binding molecule as defined above;
as combined preparation for simultaneous, separate or sequential use in the prevention or treatment of CD5+ HLA-DR+ B or T cell related diseases.

A first binding molecule can be administered prior to, concomitantly with, or subsequent to the administration of the second binding molecule to a subject which had, has, or is susceptible to have B cell disease. The CD5 binding molecules and the HLA-DR binding molecules are administered to a subject in a sequence and within a time interval such that the first binding molecule can act together with the second binding molecule to provide an increased benefit than if they were administered otherwise. Preferably, the binding molecules are administered simultaneously to the subject with a CD5+ HLA-DR+ B or T cell disorder. Also preferably, the binding molecules are administered simultaneously and every 2 or 3 weeks to said patient.

The invention also relates to an anti-CD5 antibody.

In a first embodiment of the invention, the anti-CD5 antibody comprises at least one CDR which sequence is selected from within SEQ ID NO: 1 or SEQ ID NO: 2.

In another embodiment of the invention, the anti-CD5 antibody comprises:
(i) a variable light chain comprising at least one CDR represented by a sequence selected from the group consisting of SEQ ID NO: 3, SEQ ID NO: 4, SEQ ID NO: 5 and/or
(ii) a variable heavy chain comprising at least one CDR represented by a sequence selected from the group consisting of SEQ ID NO: 6, SEQ ID NO: 7, SEQ ID NO: 8.

In another preferred embodiment of the invention, the CD5 antibody comprises a variable light chain of SEQ ID NO: 1 and/or a variable heavy chain of SEQ ID NO: 2.

The invention also relates to a HLA-DR binding molecule.

In a first embodiment of the invention, the HLA-DR antibody comprises at least one CDR which sequence is selected from within SEQ ID NO: 9 or SEQ ID NO: 10.

In another embodiment of the invention, the HLA-DR antibody comprises:
(i) a variable light chain comprising at least one CDR represented by a sequence selected from the group consisting of SEQ ID NO: 11, SEQ ID NO: 12, SEQ ID NO: 13 and/or
(ii) a variable heavy chain comprising at least one CDR represented by a sequence selected from the group consisting of SEQ ID NO: 14, SEQ ID NO: 15, SEQ ID NO: 16.

In another preferred embodiment of the invention, the HLA-DR antibody comprises a variable light chain of SEQ ID NO: 9 and/or a variable heavy chain of SEQ ID NO: 10.

EXAMPLE

Materials

The antibodies used in the present study are an anti-CD5 antibody comprising a light chain consisting in SEQ ID NO:1 and an heavy chain consisting in SEQ ID NO:2 and an anti-HLA-DR antibody comprising a light chain consisting in SEQ ID NO:9 and a heavy chain consisting of SEQ ID NO:10.

Methods

Animal experiments were performed according to the principles of laboratory animal care and French legislation. Experimental protocols were approved by the Institutional Ethics Committee for Animal Experimentation of Brittany (authorization b-2005-SL-2003). Six week old CB17 SCID mice with body weight of 18 to 22 g were purchased from Charles River Breeding Laboratories (France). Mice were kept under specific pathogen-free conditions in a separate facility using filter-topped cages and autoclaved food and bedding. All manipulations were performed in a laminar flow hood.

For inoculation, JOK-1 CD5+ tumor cells were harvested in log-phase, washed and resuspended at $10 \times 10^6$ cells/0.1 ml in phosphate-buffered saline (PBS) before being injected i.v. into the mice. Mice were randomly divided into groups and injected i.v. with antibodies alone or combined at a concentration of 10 mg/kg on days 3, 5, 7 and 11 after tumor inoculation. Mice were monitored daily for the presence of hind-leg paralysis whereupon mice were sacrificed and scored as dead.

Example 1

Anti-Leukaemia Effect and Advantage of Combining mAb in Mice

Results

The effect on mice survival of the injection of double combination of murine antibodies was observed after i.v. injection of the CD5+ transfected HLA-DR+ cell line JOK, which mimics B-CLL and mantle cell lymphoma phenotype. In particular, three double combinations: anti-CD5 and anti-CD71, anti-CD5 and anti-HLA/DR or anti-CD71 and anti-HLA/DR antibodies were analyzed. Intravenous treatment with therapeutic antibodies was initiated at various times and its effect on survival of mice was monitored.

Figure 1:
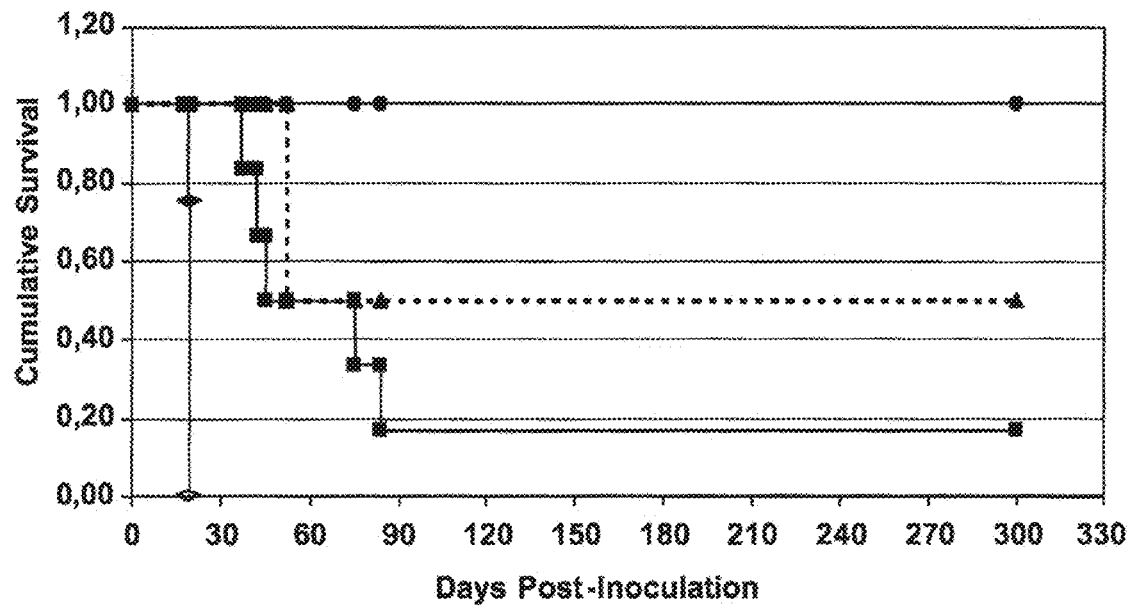
FIG. 1. depicts the survival of mice (vertically) after intravenous injection of CD5+ transfected HLA-DR+ JOK1 cells and being treated intravenously with 10 mg/kg of anti-HLA-DR and anti-CD71 antibodies (triangles), anti-CD5 and anti-HLA/DR antibodies (circles) or anti-CD5 and anti-CD71 (squares) at days 3, 5, 7 and 11. Survival was followed until day 300 after tumor injection and compared with control mice (diamonds) grafted with JOK1 5.3 cells and treated with isotype control.

It is shown that these three double combinations of murine antibodies could extend the survival of SCID mice with systemically disseminated developing B-CLL (FIG. 1). The results for each combination at day 300 are presented in Table 1.

The best combination is the combination anti-CD5 and anti-HLA/DR antibodies. In fact, at day 300 after inoculation of B-CLL cells, all mice treated with anti-CD5 and anti-HLA/DR are still alive (FIG. 1)

TABLE 1

Median survival of mice treated with the double combinations at day 300

| | Days of death | Alive mice | Median survival |
|---|---|---|---|
| Control | 19-19-19-20-20 | 0/5 | 19.5 days (19-20) |
| Combination 1 (anti-CD5+ anti-CD71) | 37-42-45-60-82 | 2/6 | 45 days |
| Combination 2 (anti-CD5+ anti-HLA/DR) | none | 6/6 | >300 |
| Combination 3 (anti-CD71+ anti-HLA/DR) | 52-53-53 | 3/6 | 52 days |

Example 2

Figure 2:
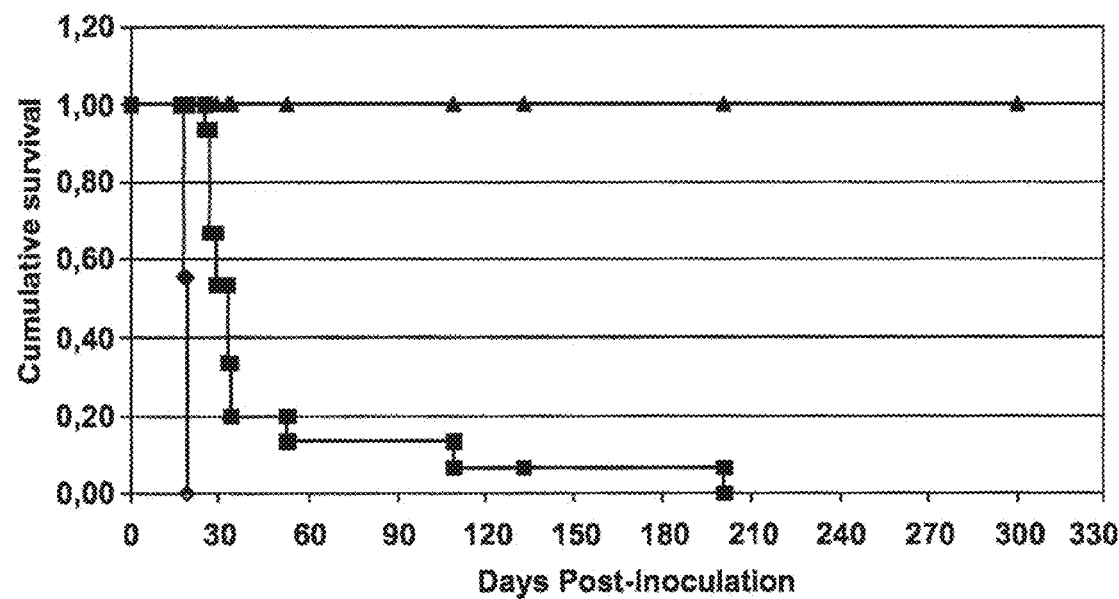
FIG. 2. depicts the survival of mice (vertically) after intravenous injection of JOK-1 CD5+ cells followed by intravenous treatment with 10 mg/kg of anti-CD5+ and anti-HLA/DR antibodies (triangles) or Rituximab (squares) at day 3, 5, 7 and 11 Survival was followed until day 300 after tumor injection and compared with control mice (circles) grafted with JOK1 5.3 cells and treated with isotype control.

Anti-Leukaemia Effect of Anti-CD5 and Anti-HLA/DR Combination Compared to Rituximab Results By day 19, all of the control treated mice had succumbed to the disseminated B-CLL, the median survival was 19 days (FIG. 2).

The results obtained with the combinations of anti-CD5 and anti-HLA-DR were compared to those obtained with an antibody presently used for therapeutic treatment of B-CLL (Rituximab). By day 300 after injection of B-CLL cells, all mice treated with anti-CD5 and anti-HLA-DR are alive compared to Rituximab-treated mice (FIG. 2), which were all dead after.

Thus, these results demonstrate that murine anti-CD5 combined with murine anti-HLA/DR have a high therapeutic advantage, even when compared to present treatment with anti-CD20 Rituximab.

---

The invention claimed is:

1. A method of treating CD5+ HLA-DR+ B or T cell related diseases in a subject in need thereof, comprising the step of administering to said subject at least one CD5 antibody and at least one HLA-DR antibody,
   wherein said at least one CD5 antibody comprises:
   (i) a variable light chain comprising the CDR1 (L1) of sequence SEQ ID NO: 3, the CDR2 L2 of sequence CDR3 L3 of sequence SEQ ID NO: 5 and,
   (ii) a variable heavy chain comprising the CDR1 (H1) of sequence SEQ ID NO: 6, the CDR2 (H2) of sequence SEQ ID NO: 7, and the CDR3 (H3) of sequence SEQ ID NO: 8, and
   wherein said at least one HLA-DR antibody comprises:
   (i) a variable light chain comprising the CDR1 (L1) of sequence SEQ ID NO: 11, a CDR2 (L2) of sequence SEQ ID NO: 12, and a CDR3 (L3) of sequence SEQ ID NO: 13 and,
   (ii) a variable heavy chain comprising the CDR1 (H1) of sequence SEQ ID NO: 14, a CDR2 (H2) of sequence SEQ ID NO: 15, and a CDR3 (H3) of sequence SEQ ID NO: 16.

2. The method of claim 1, wherein the at least one CD5 antibody and the at least one HLA-DR antibody are constituents of a bispecific antibody.

3. The method of claim 1, wherein the at least one CD5 antibody comprises a variable heavy chain of SEQ ID NO: 2.

4. The method of claim 1, wherein the at least one HLA-DR antibody comprises a variable heavy chain of SEQ ID NO: 10.

5. The method of claim 1, wherein the CD5+ HLA-DR+ B or T cell related disease is selected from the group consisting of B or T cell malignancies, B or T cell autoimmune diseases, transplantation diseases and graft rejections.

6. The method of claim 1, wherein said at least one CD5 antibody and at least one HLA-DR antibody are administered in combination with at least one other compound for the treatment of at least one CD5+ HLA-DR+ B or T cell related disease selected from the group consisting of B or T cell malignancies, autoimmune diseases, transplantation diseases and graft rejections.

7. The method of claim 1, wherein the at least one CD5 antibody comprises a variable light chain of SEQ ID NO: 1 and a variable heavy chain of SEQ ID NO: 2.

8. The method of claim 1, wherein the at least one HLA-DR antibody comprises a variable light chain of SEQ ID NO: 9 and a variable heavy chain of SEQ ID NO: 10.

9. The method of claim 1, wherein the at least one CD5 antibody comprises a variable light chain of SEQ ID NO: 1.

10. The method of claim 1, wherein the at least one HLA-DR antibody comprises a variable light chain of SEQ ID NO: 9.

* * * * *